United States Patent [19]

Annamalai

[11] Patent Number: 4,775,831
[45] Date of Patent: Oct. 4, 1988

[54] IN-LINE DETERMINATION OF PRESENCE OF LIQUID PHASE MOISTURE IN SEALED IC PACKAGES

[75] Inventor: Nagappan K. Annamalai, Nashua, N.H.

[73] Assignee: The United States of America as represented by the Secretary of the Air Force, Washington, D.C.

[21] Appl. No.: 864,222

[22] Filed: May 19, 1986

[51] Int. Cl.⁴ ............................................. G01R 27/02
[52] U.S. Cl. ................................ 324/61 R; 324/65 R
[58] Field of Search ............... 324/61 R, 65 R, 61 P; 173/73; 357/75

[56] References Cited

U.S. PATENT DOCUMENTS

| | | | |
|---|---|---|---|
| 3,479,862 | 11/1969 | Trapp et al. | 73/49.3 |
| 3,943,557 | 3/1976 | Frazee et al. | 357/75 |
| 4,050,048 | 9/1977 | Frazee | 338/35 |
| 4,224,565 | 9/1980 | Sosniak . | |
| 4,272,986 | 6/1981 | Lowry et al. | 73/73 |

Primary Examiner—Roy N. Envall, Jr.
Assistant Examiner—Leon K. Fuller
Attorney, Agent, or Firm—William G. Auton; Donald J. Singer

[57] ABSTRACT

Liquid-phase moisture is detected in sealed integrated circuit packages by measuring the conductance and capacitance of the integrated circuit at a temperature which is above temperatures which allow moisture to condense; and remeasuring the conductance and capacitance of the integrated circuit at a temperature which allows any moisture present to condense on the integrated circuit. The conductance of the integrated circuit is expected to rise sharply with the condensation of water on its surface.

4 Claims, 2 Drawing Sheets

NO WATER

WATER PRESENT

NO WATER

WATER PRESENT

IN-LINE DETERMINATION OF PRESENCE OF LIQUID PHASE MOISTURE IN SEALED IC PACKAGES

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to moisture detection systems, and more specifically to a technique and apparatus for detecting the presence of liquid phase moisture in sealed integrated circuits (IC).

It is well known that various types of device failures are attributable to the presence of moisture. Thus, for example, in sealed packages containing microelectronic devices of the integrated-circuit type, a water vapor concentration as low as several thousand parts per million can cause device failures. Accordingly, efforts have been directed at devising techniques for detecting the moisture within such a package. By detecting this moisture during the device fabrication process, it is possible initially to identify and reject failure-prone sealed packages.

The task of detecting water in sealed IC packages is alleviated by the systems disclosed in the following U.S. Patents, the disclosures of which are incorporated herein by reference:

U.S. Pat. No. 3,479,862 issued to Trapp et al;
U.S. Pat. No. 3,943,557 issued to Frazee et al;
U.S. Pat. No. 4,050,048 issued to Frazee;
U.S. Pat. No. 4,224,565 issued to Sosniak et al; and
U.S. Pat. No. 4,272,986 issued to Lowry et al.

Lowry et al disclose in-situ monitoring of the moisture content of a hermetically sealed integrated circuit package by measuring the dew point of the sealed environment. The dew point is determined by lowering the temperature of the cavity at a slow, controlled rate while the surface conductivity of a conductor pattern is monitored. As the dew point temperature of the cavity environment is approached, micro-droplets of water will condense on the surface of the sensor. The sensor comprises inter-digitized aluminum conductors on a silicon oxide surface. Sosniak et al also disclose a dew point sensor for determining the moisture content of sealed integrated circuit packages.

Frazee et al are concerned with a humidity sensor for hermetically sealed semiconductor packages. The patented sensor has low resistivity and may be either a discrete humistor or may be incorporated in the semiconductor package as an integral device. A similar humidity sensor is shown in the Frazee patent. In Trapp et al the electrical resistance between two conductors on the exterior of a package is measured to determine the presence of liquid within the package.

All the other patents cited above are exemplary in the art, and are useful for moisture determination in IC packages, but all of them use a special separate sensor rather than the IC chip itself. The presence of moisture affects the electrical characteristics of integrated circuits, and a need exists to detected moisture by these changes of electrical characteristics rather than indulging in the expense of exotic humidity sensors. The present invention is intended to satisfy that need.

SUMMARY OF THE INVENTION

The present invention includes an apparatus and a process for detecting moisture in sealed IC packages from the effect of such moisture upon the electrical characteristics of the device.

The principle of the present invention is derived from the following observation. When the conductance of an IC is measured as a function of temperature across two selected pins in the absence of moisture, a decrease in conductance is seen as the temperature decreases. When moisture is present in the form of water, conductance will exhibit a sharp increase. Moisture present in the package condenses on the chip when it is cooled. Hence, a change in the conductance slope from positive to negative with respect to temperature, as the chip is cooled, indicates the presence of moisture in the liquid phase. Similarly, the conductance will decrease sharply when the water freezes. The presence of moisture is revealed by taking comparative measurements of conductance while cooling and heating the integrated circuit. The four sharp transitions are the following: (i) water condensing on the chip; (ii) the super cooled water freezing into ice; (iii) ice melting into water; and (iv) water evaporating into the cavity. The change in conductance is quite large compared to the change in capcitance when moisture is present in the package.

Therefore, the process of the present invention includes the steps of: varying the ambient temperature around an IC; measuring the electrical characteristics of the IC; and using the measurements to determine the presence of moisture in the IC.

One embodiment of the apparatus of the present invention en tai ls a moisture measuring circuit which includes: a function generator, a pre-amplifier; and a lock-in amplifier (LIA). The function generator sends a test signal to the IC and a reference signal to the LIA. The pre-amplifier is connected in a series circuit between the IC and the LIA and conducts the IC output to the LIA. A moisture measuring system using the circuit described above would include a temperature control system and an electrical meter. The in-phase meter reading across the LIA, which is in d.c. voltage, yields a reading proportional to the IC conductance; and the quadrature reading across the LIA is proportional to the IC capacitance.

It is an object of the present invention to detect the presence of moisture in IC packages.

It is another object of the present invention to use the changes in electrical characteristics of IC packages which correspond to changes in ambient temperature to detect the presence of moisture in IC packages.

These objects together with other objects, features and advantages of the invention will become more readily apparent from the following detailed description when taken in conjunction with the accompanying drawings wherein like elements are given like reference numerals throughout.

DETAILED DESCRIPTION OF THE PREFERRED EMBODIMENT

The present invention is an apparatus and a process for detecting moisture in sealed IC packages from the effect of such moisture on the electrical characteristics of the IC in the presence of changing ambient temperature conditions.

Figure 1:
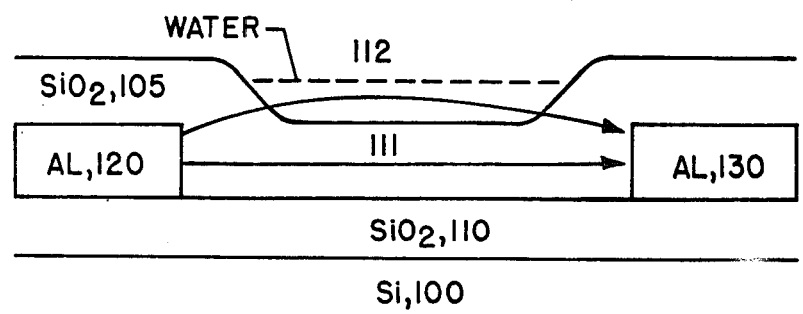
FIG. 1 is an illustration of a conventional integrated circuit which indicates the changes in the conduction path when water condenses on the integrated circuit.

The reader's attention is now directed towards FIG. 1, which is an illustration of an $SiO_2$ integrated circuit. The IC of FIG. 1 is a simplified version of a conventional design containing: a silicon substrate 100; a $SiO_2$ layer 110, two aluminum ohmic contacts 120 and 130; and a top layer of $SiO_2$ 150. The semiconductor layers are conventionally doped to form a functioning circuit in which the conduction path 111, when water is absent, flows between the ohmic contacts 120 and 130. When liquid phase water is present on the surface of the IC, the second conduction path 112, to some extent, is followed.

A more detailed discussion of semiconductor design considerations and operating characteristics, in the absence of moisture, may be found in a text by B.G. Streetman entitled "Solid State Electronic Devices", 2nd ed. (Prentice Hall, Englewood Cliffs, N.J. 1980). The effect of liquid phase moisture on the electrical characteristics of integrated circuits is more clearly understood with the help of FIGS. 2A, 2B, 3A and 3B.

Figure 2A:
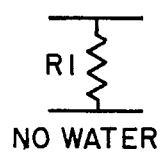
FIGS. 2A and 2B are circuit diagrams which depict the change in resistance of an integrated circuit when water condenses on it.
Figure 2B:
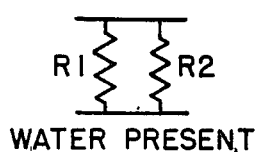

As indicated in the above-cited Streetmen reference, IC circuits can simulate electrical circuits containing a variety of electrical components including resistors, capacitors and transistors. FIGS. 2A and 2B are circuit illustrations which are intended to depict the change in impedance of an IC resistor in the presence of water. FIG. 2A is an electrical schematic of the electrical equivalent of an IC resistor without liquid phase water, and FIG. 2B depicts the same circuit with water present. As indicated by FIG. 2B, when liquid phase water coats a resistor R1 in the form of the IC of FIG. 1, it is the equivalent of adding a parallel resistor R2.

Figure 3A:
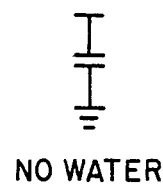
FIGS. 3A and 3B are circuit diagrams which indicate the change in impedance of an IC capacitor when water condenses on it.
Figure 3B:
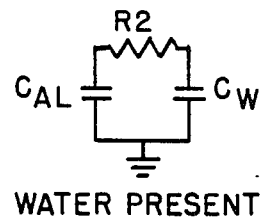

FIGS. 3A and 3B are electrical schematics of the electrical equivalents of an IC capacitor both without water (FIG. 3A) and with water (FIG. 3B).

Figure 4:
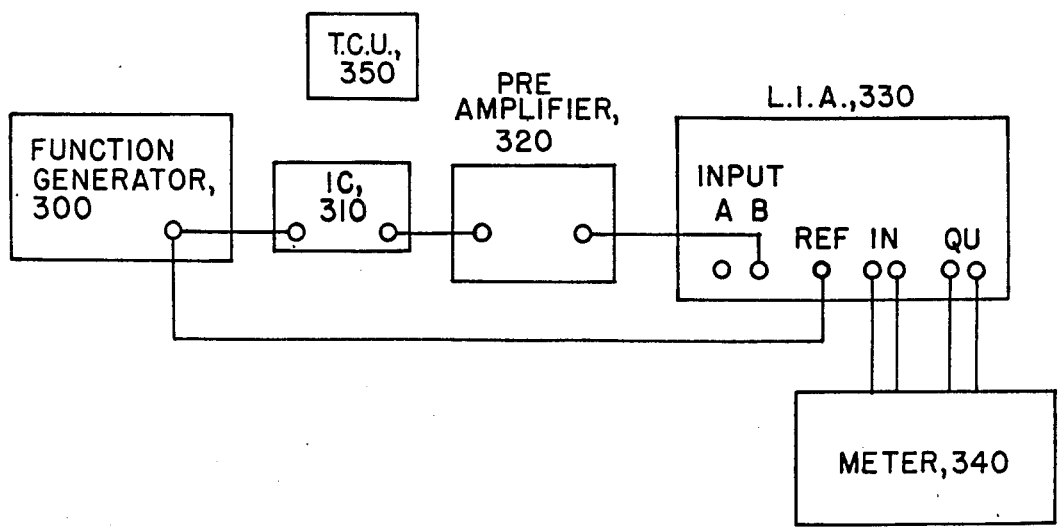
FIG. 4 is a block diagram of the moisture detection system of the present invention.

FIG. 4 is a block diagram of the moisture detection system of the present invention.

Conceptionally, the system of FIG. 4 provides a moisture detection system which detects a presence of moisture in sealed integrated circuit packages by inputting an electric test signal through the integrated circuit and measuring an output signal of the integrated circuit for moisture-induced changes in electrical characteristics of the integrated circuit corresponding with a presence of changes in ambient temperature. The moisture detection system is external to the IC, and uses the function generator 300 as a means for generating an electric test signal, which is injected into the integrated circuit 310, and a reference signal for comparison with the output signal of the integrated circuit.

In FIG. 4, the pre-amplifier 320, lock-in amplifier 330, and meter 340 serve as a measuring system, which receives the reference signal from the function generator 300, and compares it with output signal of the integrated circuit in the presence of changes of ambient temperature to detect the presence of moisture in the integrated circuit.

As discussed below, the pre-amplifier 320 of FIG. 4 is electrically connected to the integrated circuit, and produces an amplified signal by amplifying the output signal of the integrated circuit.

The lock-in amplifier 330 is electrically connected with the function generator and the pre-amplifier to receive the reference signal and the amplified signal. The lock-in amplifier can output an in-phase signal and can output a quadrature signal. If the lock-in amplifier outputs the in-phase signal, this signal is in-phase with the reference signal. The quadrature signal is 90 degrees out of phase with the reference signal.

The meter is electrically connected to and receives the in-phase and quadrature signals from the lock-in amplifier during the changes in ambient temperature. The meter indicates the change of electrical characteristics of changing conductance of the integrated circuit by measuring the in-phase signal and indicates an increase in conductance of the integrated circuit at the ambient temperatures which allow the moisture to condense upon the integrated circuit. The meter 340 also indicates the presence of moisture by measuring the capacitance of the integrated circuit by measuring the quadrature signal, and indicates a small increase in capacitance at ambient temperatures in which water condenses.

The description presented above is the general concept of the moisture detection system of FIG. 4. A more detailed description of the preferred embodiment is presented below.--

In this system, a function generator 300 provides a maximum signal voltage of 100 mV at 100 Hz. This voltage is applied to the appropriate leads of the device under test 310. The output current from the device is connected to the input terminal of a current sensitive preamplifier 320. The output of the preamplifier, which is proportional to the current, is an a.c. voltage. This voltage is fed to the input terminal of the lock-in-amplifier 330. A reference input for the LIA 330 is provided with a connection from the function generator 300. The in-phase meter reading of the LIA, which is in d.c. voltage form, is proportional to the IC conductance, and the quadrature reading is proportional to the IC capacitance. These are read by the meter 330, while a temperature control unit 350 incrementally adjusts the temperature around the IC 310 in the manner described below.

The conductance method of the present invention measures the IC conductance and capacitance at a low frequency (100Hz) and at a low voltage (100mV) by employing a lock-in-amplifier. The change in conductance is quite large compared to the change in the capacitance when moisture is present in the package.

Conductance measurement is made between two pins connected to metallization tracks adjacent to each other. These metallization tracks 120 and 130 (as shown in FIG. 1 ) lie on top of silicon dioxide 110 and connect silicon devices. A top silicon dioxide layer 150 protects the metallization lines 120 and 130. These lines are separated from each other by silicon dioxide and possibly by some silicon circuit elements. When the conductance is measured as a function of temperature across two selected pins in the absence of moisture, a decrease in conductance is seen as the temperature decreases. This is due to the change in resistivity of $SiO_2$ and junction leakage current characteristics as a function of temperature. When moisture is present in the form of water, conductance will exhibit a sharp increase. Moisture present in the package condenses on the chip when it is cooled. Hence, a change in the conductance slope from positive to negative with respect to temperature, as the chip is cooled, indicates the presence of moisture in the liquid phase.

On further cooling, water remains in a supercooled state until it freezes. The conductance will decrease sharply when the water freezes. Beyond this point, the slope of the conductance versus temperature curve is positive due to the changes in the resistivity of $SiO_2$ and junction leakage current. When the cooling is stopped and the device temperature is allowed to increase, the ice melts at 0° C. producing a sharp increase in conductance. On further increase in temperature, water evaporates into the cavity. The presence of moisture in the liquid phase is revealed by four sharp transitions when a device is taken through one cycle of cooling and heating. The four sharp transitions are the following: (i) water condensing on the chip, (ii) the super cooled water freezing into ice, (iii) ice melting into water and (iv) water evaporating into the cavity. The first two sharp transitions occur during the cooling cycle and the last two sharp transitions during the heating cycle.

A sharp increase in conductance as opposed to capacitance can be understood by referring back to FIG. 1. In the absence of water, conductance is due to the path between metal tracks 1. When water condenses, conductance is due to paths 1 and 2. The conductance shows a sharp rise due to the path 2 introduced from the moment water starts condensing on the integrated circuit. A capacitance increase is due to additional capacitance introduced between the water layer and silicon substrate.

From the description provided above, the present invention is normally used as part of a process of detecting moisture in a sealed integrated circuit. This process comprises the steps of:

providing an ambient temperature around the integrated circuit which is above the temperature at which moisture condenses;

measuring electrical characteristics of the integrated circuit;

setting the ambient temperature to a temperature at which moisture condenses;

remeasuring the electrical characteristics of the integrated circuit; and detecting changes in the electrical characteristics of the integrated circuit which indicate the presence of moisture.

The measuring step of the process is composed of the following substeps:

injecting a first test signal into the integrated circuit to cause it to produce a first output signal which indicates its electrical characteristic in the absence of liquid-phase moisture;

generating a first reference signal for comparison with the first output signal; and outputting a first in-phase signal which is an in-phase signal between the first reference signal and the first output signal, this first in-phase signal being proportional to the conductance of the integrated circuit in the absence of moisture.

The remeasuring step of the process is composed of the following substeps:

injecting a second test signal into the integrated circuit to cause it to produce a second output signal which indicates its electrical characteristics as affected by any liquid-phase moisture present which has condensed on the integrated circuit;

generating a second reference signal for comparison with the second output signal; and outputting a second in-phase signal which is an in-phase signal between the second reference signal and the second output signal, this second in-phase signal being proportional to the conductance of the integrated circuit and rising sharply above the first in-phase signal in the event of the presence of liquid-phase moisture on the integrated circuit.

In the process described above, the detecting step comprises making a comparison between the first and second in-phase signals and indicating a presence of liquid-phase moisture if said second in-phase signal has an amplitude which has risen sharply above that of the first in-phase signal. The measuring step includes a generation of a first quadrature signal between the first reference signal and the first output signal, this first quadrature signal being an indication of the capacitance of the integrated circuit in the absence of moisture.

When the process is conducted as described above, the remeasuring step includes a generation of a second quadrature signal between the second reference signal and the second output signal, this second quadrature signal being an indication of the capacitance of the integrated circuit in the presence of any liquid-phase moisture which has condensed on the integrated circuit. Additionally, the detecting step includes a comparison between the first and second quadrature signals to determine if the capacitance of the integrated circuit has experiences any moisture-induced change.

Figure 5:
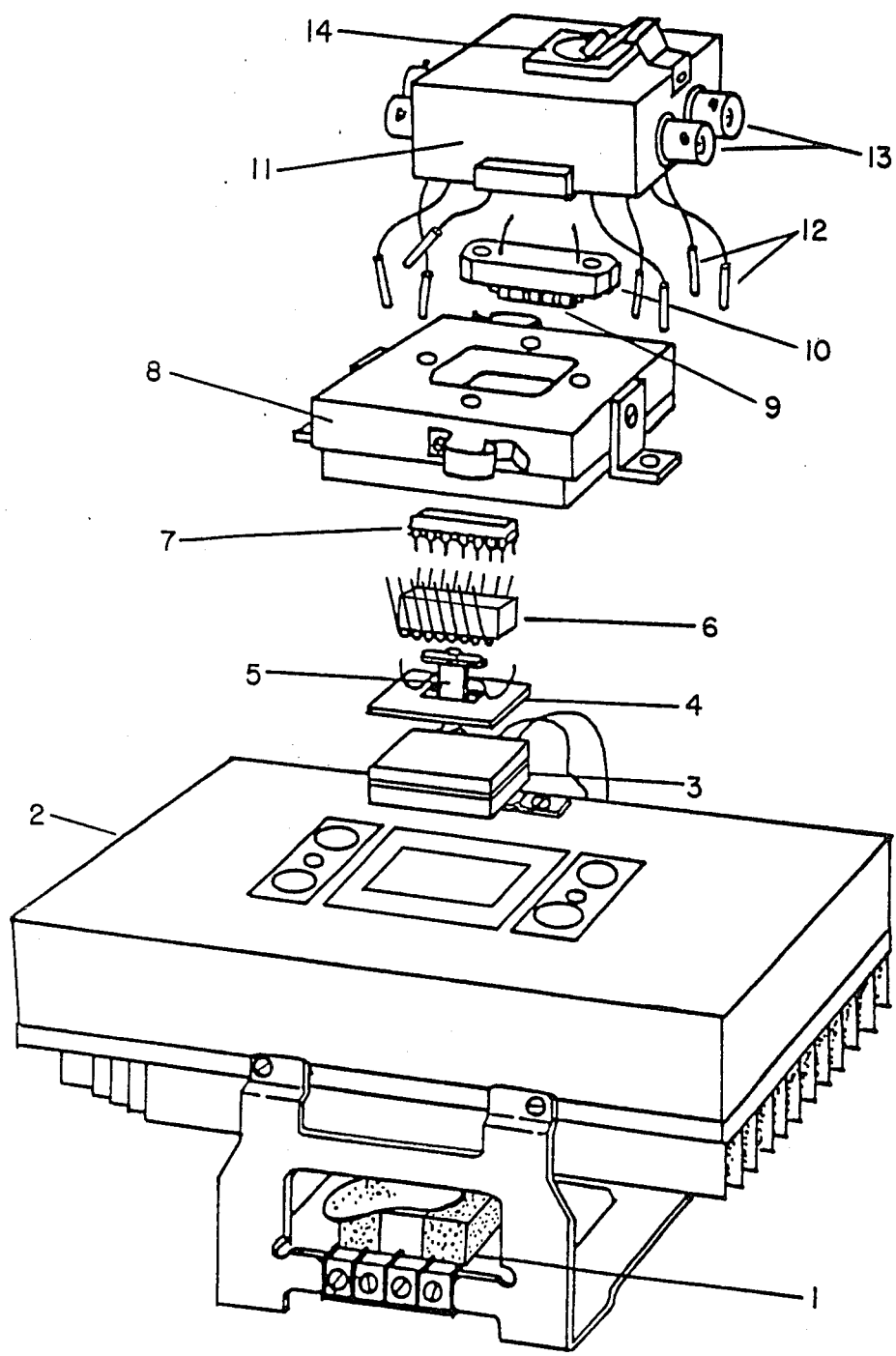
FIG. 5 is an illustration of the moisture detection system of the present invention.

FIG. 5 is an illustration of an embodiment of the IC moisture detection system of the present invention. A cooling fan 1 and a heat sink 2 ensure the heat extraction from the thermoelectric coolers 3. The thermoelectric coolers are used for cooling the device. The metal finger 4 is used for cooling the device. The metal finger with a base plate sits on top of the cooler. A diode used to monitor the temperature is embedded into this finger 5. A wire wrap socket 6 is used for inserting the device 7. A plexiglass platform 8 encloses the thermoelectric coolers and has an opening in the middle to accommodate the metal finger and the device. A resistor 9 embedded into the cross piece 10 is used to heat the top lid of the package. The cross piece is secured to the base plexiglass plate by screws, and presses down the package to make firm contact with the metal finger. A plexiglass box 11 has provisions for internal connections 12 to the device and external connections 13 to the lock-in-amplifier, diode, and heater power.

The plexiglass box is provided with a window 14 on the top. To allow the desired moisture level to be established inside this plexiglass box the whole assembly is placed inside an environmental chamber. The plexiglass box setup of FIG. 5 is useful for demonstration of the effects of varying moisture levels. This in-process test setup measures the conductance of an IC as function of temperature of sealed devices from the manufacturing line.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A moisture detection system which detects a presence of moisture in sealed integrated circuit packages by inputting an electric test signal through the sealed integrated circuit and measuring an output signal of the sealed integrated circuit for moisture-induced changes in electrical characteristics of the sealed integrated circuit corresponding with a presence of changes in ambient temperature, said moisture detection system being external to the integrated circuit and comprising;

a means for generating said electric test signal, said generating means being electrically connected with and external to the sealed integrated circuit and injecting said electric test signal into said sealed integrated circuit said generating means also producing a reference signal for comparison with the output signal of the integrated circuit;

a pre-amplifier which is electrically connected with and external to the sealed integrated circuit and which produces an amplified signal by amplifying the output signal of the sealed integrated circuit;

a lock-in amplifier which is electarically connected with said generating means and said pre-amplifier to receive said reference signal and said amplified signal, said lock-in amplifier outputting an in-phase signal ; and a meter which is electrically connected to and receives said in-phase signal from said lock-in amplifier during said changes in ambient temperature, said meter indicating the change of electrical characteristics of changing conductance of the sealed integrated circuit by measuring the in-phase signal and indicating an increase in conductance of the integrated circuit at the ambient temperatures which allow the moisture to condense upon sealed integrated circuit .

2. A moisture detection system, as defined in claim 1, including a means of controlling the ambient temperature around the integrated circuit to allow measurements to be taken at temperatures above which moisture condenses, and subsequently to allow measurements to be taken of the electrical characteristics of the integrated circuit at temperatures where moisture condenses on the integrated circuit, said controlling means thereby allowing a comparison of the electrical characteristics of the integrated circuit to indicate the presence of liquid-phase moisture in the integrated circuit.

3. A moisture detection system which detects a presence of moisture in a sealed integrated circuit by inputting an electric test signal through the sealed integrated circuit and measuring an output signal of the sealed integrated circuit for moisture-induced changes in electrical characteristics of the integrated circuit corresponding with a presence of changes in ambient temperature, said moisture detection system being external to the sealed integrated circuit and comprising:

a means for generating said electric test signal, said generating means being electrically connected with and external to the sealed integrated circuit, and injecting said electric test signal into said sealed integrated circuit, said generating means also producing a reference signal for comparison with the output signal of the sealed integrated circuit;

a pre-amplifier which is electrically connected with and external to the sealed integrated circuit, and which produces an amplified signal by amplifying the output signal of the sealed integrated circuit;

a lock-in amplifier which is electrically connected with said generating means and said pre-amplifier to receive said reference signal and said amplified signal; said lock-in amplifier outputting a quadrature signal; and a meter which is electrically connected to and which receives said quadrature signal from said lock-in amplifier during said changes in ambient temperature, said meter indicating the change of electrical characteristics of changing conductance of the sealed integrated circuit by measuring the capacitance of the sealed integrated circuit by measuring the quadrature signal and indicating a small increase capacitance at ambient temperatures in which water condenses.

4. A moiture detection system, as defined in claim 3, including a means of controlling the ambient temperature around the sealed integrated circuit to allow measurements to be taken at temperatures above which moisture condenses, and subsequently to allow measurements to be taken of the electrical characteristics of the sealed integrated circuit at temperatures where moisture condenses on the integrated circuit, said controlling means thereby allowing a comparison of the electrical characteristics of the sealed integrated circuit to indicate the presence of liquid-phase moisture in the integrated circuit

* * * * *